(12) United States Patent
Dorsel et al.

(10) Patent No.: US 7,018,842 B2
(45) Date of Patent: Mar. 28, 2006

(54) READING DRY CHEMICAL ARRAYS THROUGH THE SUBSTRATE

(75) Inventors: Andreas N. Dorsel, Menlo Park, CA (US); John F. Corson, Stanford, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 688 days.

(21) Appl. No.: 10/087,447

(22) Filed: Feb. 28, 2002

(65) Prior Publication Data

US 2003/0160183 A1    Aug. 28, 2003

(51) Int. Cl.
G01N 21/64    (2006.01)

(52) U.S. Cl. .................... 436/86; 436/94; 436/165; 436/172

(58) Field of Classification Search ............ 436/164, 436/165, 172, 94, 86, 89; 422/82.05, 82.08, 422/82.11; 356/445; 435/6, 7.1, 518
See application file for complete search history.

(56) References Cited

U.S. PATENT DOCUMENTS

| | | | | |
|---|---|---|---|---|
| 4,608,344 A | * | 8/1986 | Carter et al. ................... | 436/34 |
| 4,857,273 A | * | 8/1989 | Stewart .................... | 422/82.11 |
| 5,341,215 A | * | 8/1994 | Seher ......................... | 356/445 |
| 5,485,277 A | * | 1/1996 | Foster ........................ | 356/445 |
| 5,508,200 A | * | 4/1996 | Tiffany et al. ................ | 436/44 |
| 5,585,639 A | | 12/1996 | Dorsel et al. | |
| 5,599,668 A | * | 2/1997 | Stimpson et al. .............. | 435/6 |
| 5,675,443 A | | 10/1997 | Dorsel | |
| 5,763,870 A | | 6/1998 | Sadler et al. | |
| 5,834,758 A | | 11/1998 | Trulson et al. | |
| 5,874,219 A | | 2/1999 | Rava et al. | |
| 5,945,679 A | | 8/1999 | Dorsel et al. | |
| 6,177,990 B1 | | 1/2001 | Kain et al. | |
| 6,232,072 B1 | * | 5/2001 | Fisher ........................... | 435/6 |
| 6,238,862 B1 | | 5/2001 | McGall et al. | |
| 6,627,397 B1 | * | 9/2003 | Nakamura et al. ............. | 435/6 |
| 6,791,690 B1 | * | 9/2004 | Corson et al. ............. | 356/445 |
| 6,800,439 B1 | * | 10/2004 | McGall et al. ................. | 435/6 |
| 2005/0037365 A1 | * | 2/2005 | Anvar et al. ................... | 435/6 |

* cited by examiner

*Primary Examiner*—Jeffrey R. Snay
(74) *Attorney, Agent, or Firm*—Gordon Stewart

(57) ABSTRACT

A method of interrogating an addressable array unit having a transparent substrate with a back surface, and an array with a plurality of different chemical features on a front surface. The method may include illuminating the features while the array is dry, with an interrogating light which is directed through the substrate from the back surface and onto the chemical features on the front surface. The light emitted from respective features in response to the interrogating light may be detected, which detected light has passed from the front surface, through the substrate and out the back surface. In one arrangement the light is emitted from locations of the features which are spaced from the front surface a distance of less than one-eighth of the wavelength of the illuminating light in a gas or a vacuum which is in contact with the dry array. Other methods and a package containing an addressable array are also provided.

13 Claims, 4 Drawing Sheets

READING DRY CHEMICAL ARRAYS THROUGH THE SUBSTRATE

FIELD OF THE INVENTION

This invention relates to arrays, particularly biopolymer arrays such as DNA or protein arrays, which are useful in diagnostic, screening, gene expression analysis, and other applications.

BACKGROUND OF THE INVENTION

Polynucleotide arrays (such as DNA or RNA arrays) and peptide array, are known and may be used, for example, as diagnostic or screening tools. Such arrays include regions (sometimes referenced as spots or features) of usually different sequence polynucleotides or peptides arranged in a predetermined configuration on a substrate. The array is "addressable" in that different features have different predetermined locations ("addresses") on a substrate carrying the array.

Biopolymer arrays can be fabricated using in situ synthesis methods or deposition of the previously obtained biopolymers. The in situ fabrication methods include those described in U.S. Pat. No. 5,449,754 for synthesizing peptide arrays, and in U.S. Pat. No. 6,180,351 and WO 98/41531 and the references cited therein for polynucleotides. In situ methods also include photolithographic techniques such as described, for example, in WO 91/07087, WO 92/10587, WO 92/10588, and U.S. Pat. No. 5,143,854. The deposition methods basically involve depositing biopolymers at predetermined locations on a substrate which are suitably activated such that the biopolymers can link thereto. Biopolymers of different sequence may be deposited at different feature locations on the substrate to yield the completed array. Procedures known in the art for deposition of biopolymers, particularly DNA such as whole oligomers or cDNA, are described, for example, in U.S. Pat. No. 5,807,522 (touching drop dispensers to a substrate), and in PCT publications WO 95/25116 and WO 98/41531, and elsewhere (use of a pulse jet in the form of a piezoelectric inkjet head).

Further details of large scale fabrication of biopolymer arrays by depositing either previously obtained biopolymers or by the in situ method, are disclosed in U.S. Pat. No. 6,242,266, U.S. Pat. No. 6,232,072, U.S. Pat. No. 6,180,351, and U.S. Pat. No. 6,171,797.

In array fabrication, the quantities of DNA available for the array are usually very small and expensive. Sample quantities available for testing are usually also very small and it is therefore desirable to simultaneously test the same sample against a large number of different probes on an array. These conditions require the manufacture and use of arrays with large numbers of very small, closely spaced features.

The arrays, when exposed to a sample, will exhibit a binding pattern. The array can be read by observing this binding pattern by, for example, labeling all targets such as polynucleotide targets (for example, DNA), in the sample with a suitable label (such as a fluorescent compound), scanning an illuminating beam across the array and accurately detecting the fluorescent signal from the different features of the array. Assuming that the different sequence polynucleotides were correctly deposited in accordance with the predetermined configuration, then the observed binding pattern will be indicative of the presence and/or concentration of one or more polynucleotide components in the sample. Peptide or arrays of other chemical moieties can be used in a similar manner. Conventionally, the illuminating and detecting have been performed on a dry array from a forward direction facing a front surface of the array carrying the array features, so that the illuminating and detected light need not pass through the substrate. In an alternative known arrangement, a transparent substrate forms part of a chamber in a housing with the array on a front substrate surface facing inward to the chamber. After exposure to a liquid containing the sample, the chamber is flushed and again filled with a liquid and the liquid containing chamber positioned in the array reading apparatus. In this situation, aside from the flushing and re-filling of the chamber, care must be taken that liquid does not leak from the chamber while positioned in the reading apparatus. The illuminating and detecting in this case has, of necessity, been performed in a backward direction through the substrate and onto the array while it is immersed in the liquid.

Techniques and apparatus for scanning chemical arrays are described, for example, in U.S. Pat. No. 5,763,870 and U.S. Pat. No. 5,945,679. Apparatus which reads an array by scanning an illuminating beam by the foregoing technique are often referred to as scanners and the technique itself often referred to as scanning. Conventionally, such scanning has been done by illuminating array features on a front surface of the substrate one pixel at a time.

Array scanners typically use a laser beam as a light source, which is scanned over pixels covering the array features. A detector (typically a fluorescence detector) with a very high light sensitivity is normally desirable to achieve maximum signal-to-noise in detecting hybridized molecules, particularly in array scanners used for DNA sequencing or gene expression studies. At present, photomultiplier tubes ("PMTs") are still the detector of choice although charge coupled devices ("CCDs") and avalanche photodiodes ("APDs") can also be used. PMTs and APDs are typically used for temporally sequential scanning of array features, while CCDs permit scanning many features in parallel (for example, one line of features simultaneously, in which case an illuminating line may be used).

When a sample component only weakly binds to an array feature (due to a low concentration of that component in the sample) the resulting fluorescence signal from that feature will be low. To be able to detect such low signal features, it is important to detect the resulting low signal with a high signal to noise ratio. It is also desirable to have a reading method where a liquid filled chamber containing the array is not positioned within the scanner.

SUMMARY OF THE INVENTION

The present invention then, provides in one aspect a method of interrogating an addressable array unit having a transparent substrate with a back surface, and an array with a plurality of different chemical features on a front surface. The method includes illuminating the features while the array is dry, with an interrogating light which is directed through the substrate from the back surface and onto the chemical features on the front surface. Light emitted from respective features in response to the interrogating light is detected, which detected light has passed from the front surface, through the substrate and out the back surface. The detected emitted light is emitted from locations of the features which are spaced from the front surface a distance of less than one-eighth of the wavelength of the illuminating light (and optionally less than one-twentieth, less than one-fortieth, or less than one-fiftieth of the wavelength of the illuminating light). The foregoing wavelengths are measured in a gas (such as air or nitrogen), or a vacuum, whichever one is in contact with the dry array during reading. For example, for many illuminating light peak emissions (such as about 530 nm or 630 nm) and different emitted light peak emissions (such as 550 nm to 610 nm, or 650 nm to 730 nm), the light may be emitted from locations which are less than 50 nm, less than 20 nm, or even less than 10 nm from the front surface of the substrate. Optionally, a method of the present invention may include, prior to the illuminating and detecting, exposing the array to a sample in a liquid, then drying the array. In an alternative configuration, the detected emitted light may be from locations which are spaced from the front surface by any of the foregoing fraction of the detected emitted light wavelength rather than the interrogating light wavelength (or the locations may satisfy the spacing requirements based on any of the foregoing fractions of both the interrogating and detected emitted light wavelengths).

In another aspect of the present invention, a dry array on a substrate may be illuminated and emitted light detected, both as described above. In this aspect though, the detected emitted light is emitted from locations of the features which are spaced from the front surface a distance such that the average detected signal from the dry array is at least 10% (or at least 20%, 40%, 60%, 80%, or at least 100%) greater than would be detected under the same conditions except with the interrogating light and detected emitted light not passing through the substrate. By "same conditions" in this context includes the same array/substrate and same instrument (and therefore with the same interrogating light illumination and emitted light detection, as well as the same depth of field for the detected emitted light, and with the focal plane adjusted to the same position relative to the front surface of the substrate).

In a method of the present invention, the interrogating light may be directed toward the back surface at an angle of less than 45 degrees to a normal to the back surface (such as less than 25, 15, or less than 5 degrees), and more than 0, 1, 2 or 4 degrees. The same ranges may be used for the detected light leaving the back surface.

Another aspect of the present invention provides a package having an addressable array unit having a transparent substrate with a back surface, and an array with a plurality of different chemical features on a front surface, which chemical features may have a thickness (measured when the array is dry) of less than 100 nm (or any other thickness mentioned herein.). Since the array may not have been exposed to a sample at this point (for example, to a sample containing many fluorescently labeled polynucleotides of different sequence which hybridize to respective polynucleotide array features), this thickness may only provide an indication of the distance by which the light emitting features will be spaced from the front surface of the substrate during reading of the dry array. The package further includes instructions to interrogate the array by a method of the present invention. For example, an identifier carried on the array substrate, or a housing carrying the substrate, may provide such instructions.

The present invention further provides a method for use with an addressable array unit having a transparent substrate with a back surface, and an array with a plurality of different chemical features on a front surface. The method includes reading (such as machine reading) an identifier associated with the array unit (such as by being present on the substrate carrying the array, a housing carrying the substrate, or in or on a same package with the array substrate). An instruction that the array should be interrogated and read through the substrate from the back surface, is retrieved (such as by a processor) based on the read identifier. The instruction may be retrieved from the read identifier itself, or from a memory using data from the read identifier (for example, the whole or part of the retrieved identifier). The retrieved instruction may be used to check that the array is properly oriented within an array reader such that the array can be interrogated and read by the reader through the substrate from the back surface.

Another aspect of the present invention provides an apparatus for reading an array which illuminates the array and detects light emitted in response thereto, through the substrate in a manner as already described. The apparatus includes a light source to provide the interrogating light, and a detector to receive the emitted light. A processor receives the data from the detector and may save the results (either further processed or raw) in a memory. The processor may also execute any other method of the present invention, such as retrieving the instruction based on the read identifier, and checking that the array is properly oriented such as based on signals received from the detector or another means (for example, based on whether an indicia, such as the identifier or other indicia, is facing in the correct direction corresponding to proper orientation of the array in the apparatus. The present invention further provides a computer program product for use with such a chemical array reader apparatus. The computer program product comprises a computer readable storage medium having a computer program stored thereon which, when loaded into the processor, causes the reader to execute a method as describe herein.

While the methods and apparatus have been described in connection with arrays of various moieties, such as polynucleotides or DNA, it will be understood throughout this description that other moieties can be used and may include any chemical moieties such as other biopolymers or polymers.

The present invention can provide any one or more of the following or other benefits. For example, a good signal to noise ratio can be obtained while not requiring fluid filled chambers to be mounted in an array reader.

BRIEF DESCRIPTION OF THE DRAWINGS

Embodiments of the invention will now be described with reference to the drawings, in which.

To facilitate understanding, the same reference numerals have been used, where practical, to designate similar elements that are common to the FIGS.

DETAILED DESCRIPTION OF THE INVENTION

Figure 1:
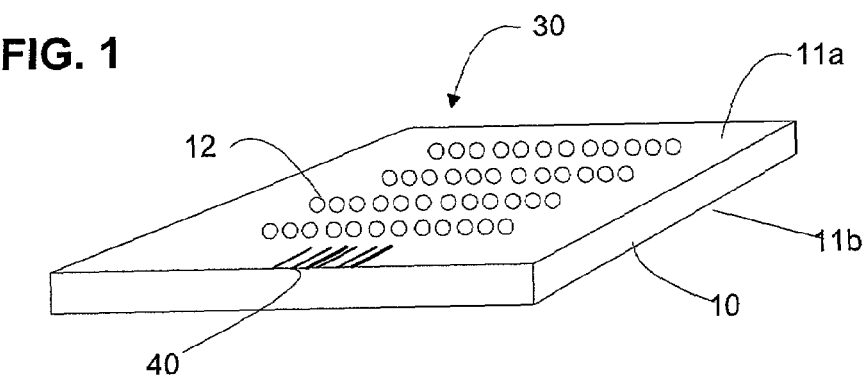
FIG. 1 is a perspective view of an array package including a substrate carrying a typical array, as may be used in the present invention.

In the present application, unless a contrary intention appears, the following terms refer to the indicated characteristics. A "biopolymer" is a polymer of one or more types of repeating units. Biopolymers are typically found in biological systems and particularly include polysaccharides (such as carbohydrates), and peptides (which term is used to include polypeptides and proteins) and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A biomonomer fluid or biopolymer fluid reference a liquid containing either a biomonomer or biopolymer, respectively (typically in solution).

An "array", unless a contrary intention appears, includes any one-, two- or three-dimensional arrangement of addressable regions bearing a particular chemical moiety or moieties (for example, biopolymers such as polynucleotide sequences) associated with those regions. An array is "addressable" in that it has multiple regions of different moieties (for example, different polynucleotide sequences) such that a region (also referenced as a "feature" or "spot" of the array) at a particular predetermined location (an "address") on the array will detect a particular target or class of targets (although a feature may incidentally detect non-targets of that feature). Note that the finite small areas on the array which can be illuminated and from which any resulting emitted light can be simultaneously (or shortly thereafter) detected, define pixels which are typically substantially smaller than a feature (typically having an area about 1/10 to 1/100 the area of a feature). Array features are typically, but need not be, separated by intervening spaces. In the case of an array, the "target" will be referenced as a moiety in a mobile phase (typically fluid), to be detected by probes ("target probes") which are bound to the substrate at the various features. However, either of the "target" or "target probes" may be the one which is to be evaluated by the other (thus, either one could be an unknown mixture of polynucleotides to be evaluated by binding with the other). An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data. An array "package" may be the array plus only a substrate on which the array is deposited, although the package may include other features (such as a housing with a chamber). A "chamber" references an enclosed volume (although a chamber may be accessible through one or more ports). It will also be appreciated that throughout the present application, that words such as "top", "upper", and "lower" are used in a relative sense only. Wavelengths are peak wavelengths unless otherwise indicated. By "transparent" is referenced a substrate which transmits at least 80% (or at least 90%, 95%, or 98%) of both the interrogating and emitted light as measured at the peak wavelengths.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station. Reference to a singular item, includes the possibility that there are plural of the same items present. "May" means optionally. Methods recited herein may be carried out in any order of the recited events which is logically possible, as well as the recited order of events. All patents and other references cited in this application, are incorporated into this application by reference except insofar as they may conflict with those of the present application (in which case the present application prevails).

Figure 2:
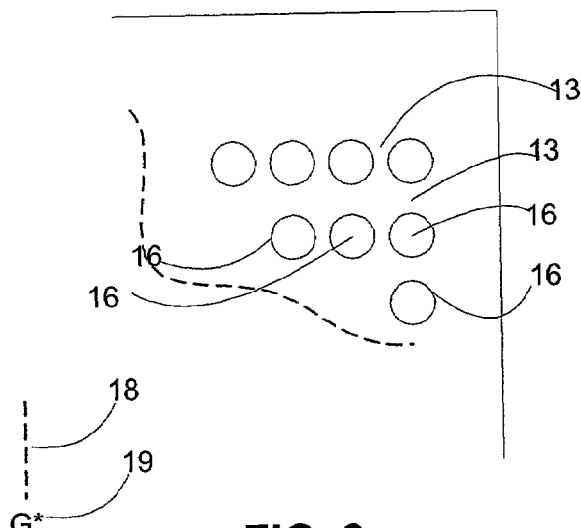
FIG. 2 is an enlarged view of a portion of FIG. 1 showing some of the identifiable individual features of a single array of FIG. 1.
Figure 3:
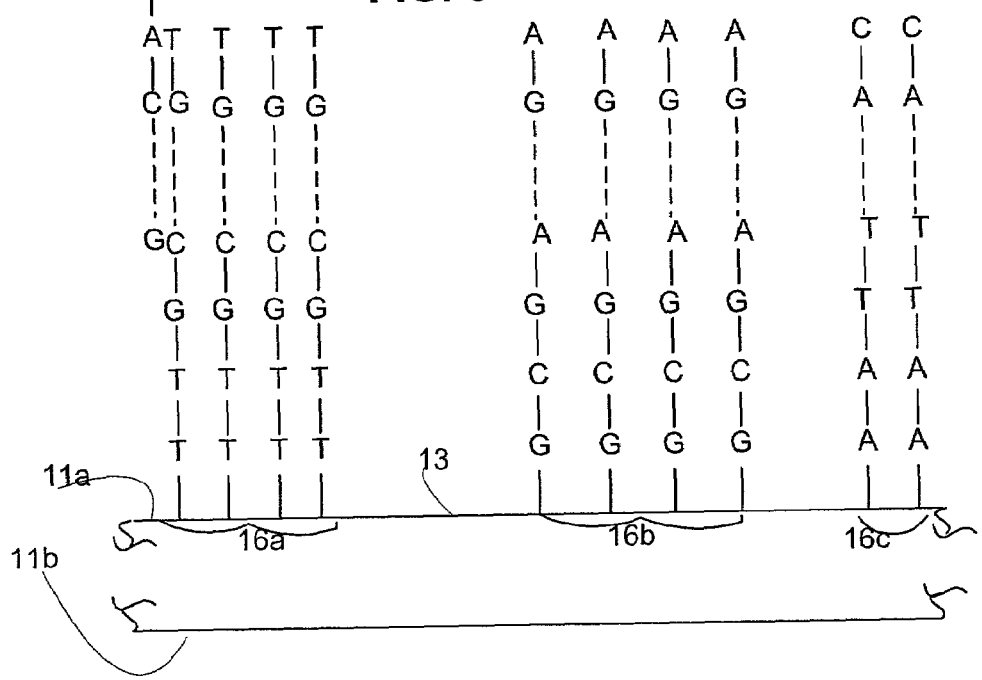
FIG. 3 is an enlarged cross-section of a portion of FIG. 2.

Referring first to FIGS. 1–3, an array unit 30 shown includes a contiguous planar transparent substrate 10 carrying multiple features 16 disposed across a front surface 11a of substrate 10 and separated by interfeature areas 13. Features 16 are disposed in a pattern which defines the array. A second surface 11b of substrate 10 does not carry any features. Substrate 10 may be of any shape although the remainder of any unit carrying substrate 10, and the apparatus of the present invention, may need to be adapted accordingly. A typical array may contain at least ten features 16, or at least 100 features, at least 1,000, at least 100,000 features, or more. All of the features 16 may be of different composition, or some could be the same (for example, when any repeats of each feature composition are excluded the remaining features may account for at least 5%, 10%, or 20% of the total number of features). Each features carries probes in the form of a one moiety or mixture of moieties, which in the case of each feature 16 in FIGS. 1–3 is a polynucleotide having a particular sequence, while interfeature areas 13 do not carry any moieties of a type the same as the features 16 (for example, no polynucleotides in the case of features 16 carrying polynucleotides). This is illustrated schematically in FIG. 3 where regions 16 are shown as carrying different polynucleotide sequences. Features 16 may have widths (that is, diameter, for a round spot) of at least 5 or 10 µm, and less than 1.0 cm. In embodiments where very small spot sizes or feature sizes are desired, each of the features 16 may have widths of at least 1.0 µm and less than 1.0 mm, usually less than 500 µm, and more usually less than 200 µm. Features which are not round may have areas equivalent to the area ranges of round features 16 resulting from the foregoing diameter ranges. The probes of features 16 are typically linked to substrate 10 through a suitable linker, not shown.

The array 12 may cover an area of less than 100 cm$^2$, or even less than 50, 10 or 1 cm$^2$. In many embodiments, substrate 10 will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm.

An array identifier 40 in the form of a bar code in FIG. 1, is associated with the array 12, by being provided on the same substrate 10 adjacent one of the arrays 12. In the case where more than one array 12 is present on the same substrate 10, a separate identifier can be provided adjacent each corresponding array 12 if desired. Identifier 40 may either contain information on the layout of array 12 as well as an instruction that the array should be interrogated and read through the substrate from the back surface, or be linkable to a file containing such information in a manner such as described in U.S. Pat. No. 6,180,351. Each identifier 40 for different arrays may be unique so that a given identifier will likely only correspond to one array 12 or to arrays 12 on the same substrate 10. This can be accomplished by making identifier 40 sufficiently long and incrementing or otherwise varying it for different arrays 12 or arrays 12 on the same substrate 10, or even by selecting it to be globally unique in a manner in which globally unique identifiers are selected as described in U.S. Pat. No. 6,180, 351.

Figure 5:
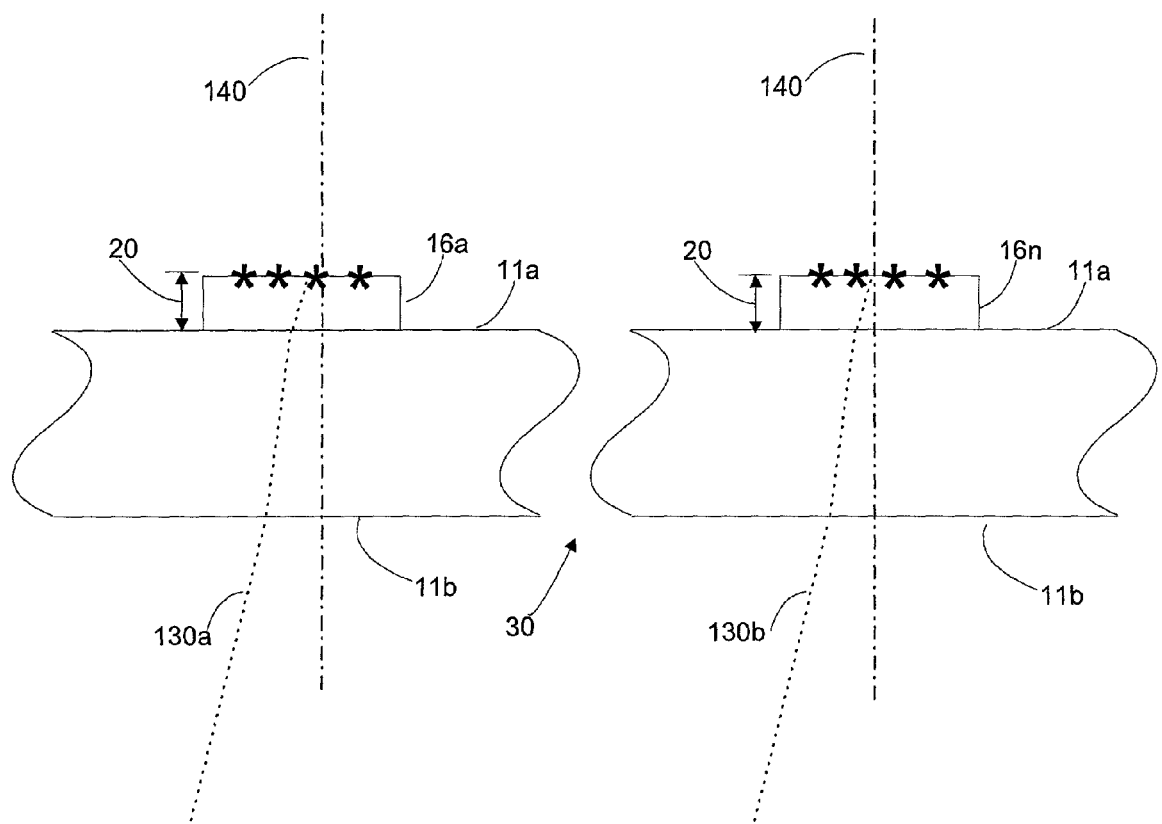
FIG. 5 illustrates components of the apparatus of FIG. 4 in more detail.

Arrays such as those of FIGS. 1–3 can be fabricated using drop deposition from pulse jets of either polynucleotide precursor units (such as monomers) in the case of in situ fabrication, or the previously obtained polynucleotide. Such methods are described in detail in, for example, the previously cited references including U.S. Pat. No. 6,242,266, U.S. Pat. No. 6,232,072, U.S. Pat. No. 6,180,351, U.S. Pat. No. 6,171,797, U.S. Pat. No. 6,323,043, U.S. patent application Ser. No. 09/302,898 filed Apr. 30, 1999 by Caren et al., and the references cited therein. As already mentioned, these references are incorporated herein by reference. Other drop deposition methods can be used for fabrication, as previously described herein. Also, instead of drop deposition methods, other array fabrication method may be used such as described in U.S. Pat. No. 5,599,695, U.S. Pat. No. 5,753,788, and U.S. Pat. No. 6,329,143. Interfeature areas 13 need not be present particularly when the arrays are made by light directed methods as described in those patents. In use, a feature can detect a polynucleotide of a complementary sequence by hybridizing to it, such as polynucleotide 18 hybridizing to, and being detected by, feature 16a in FIG. 3 (the "*" on polynucleotide 18 indicating a label 19 such as a fluorescent label). Such labels are the molecular subgroups which act as locations which emit light in response to the interrogating light, and are spaced from front surface 11a by a distance less than one-eighth, one-twentieth, or less than one-fourtieth or one-fiftieth the wavelength of the interrogating light beam. For example, this distance which may be referenced as a feature "thickness" 20 (see FIG. 5) of the probes at features 16 (which includes any detected target 18 to which probes 20 are bound), is often less than 50 nm, less than 20 nm, or even less than 10 nm from the front surface of the substrate. In the case where the array has not yet been exposed to a sample, the feature thickness may have any of the foregoing values although it will not include any target 18 (nor any labels in this situation where the target is labeled). This thickness 20 can be controlled by selecting polynucleotide or other probes, and their labeled targets (when present), at features 16 which, even if maximally extended in a straight line perpendicular to the surface, would not have a length greater than the foregoing. For example, for naturally occurring polynucleotides the spacing between adjacent complementary base pairs is about 0.35 nm. Thus, even features single-stranded probes of 100 bases in length would be less than 50 nm in thickness (not including bound target length which may extend from the end of the probes). In practice, the actual thickness is far less than this since polynucleotide probes will not stand vertical to front surface 10a nor will they be straight. For example, single-stranded probes of 60 nucleotides in length which are bound by their ends to front surface 11a will form a feature of less than 10 nm in thickness. Note that all such thicknesses as described herein are measured when the array is dry, and may be measured using atomic force microscopy. Additionally, another way to evaluate whether the light emitting locations are spaced an appropriate distance from front surface 11a together with substrate 10 having a sufficient transmittance, is in a first case to measure the average detected signal from the fluorescent labels on dry array 12 by illuminating with the interrogating light through substrate 10 and onto features 16, and detecting the resulting emitted light through substrate 10, as shown in FIG. 5. This can then be compared to the average detected signal measured in a second case under the same conditions as the first case except with the interrogating light and detected emitted light not passing through substrate 10 (that is, the interrogating light is directed from the front direction onto front surface 11a, while the emitted light is detected from a front direction also). A suitable distance is present when the average signal in the first case is at least 5% or at least 10% (or at least 20%, 40%, 60%, 80% or at least 100%) greater than obtained in the second case. The maximum distance chromophores can be from the surface can also be determined by analyzing the nucleotides constituting the molecular chain linking them to the surface and then adding the nucleotide spacings, with the option to account further for the fact that molecules are not normally straight chains using techniques known to those skilled in the art.

Substrate 10 may be of any suitable material, and is preferably sufficiently transparent to the wavelength of an interrogating and array emitted light as already described. Such transparent materials may include glass, fused silica, and appropriate plastics. The first surface 11a of substrate 10 may be modified with one or more different layers of compounds that serve to modify the properties of the surface in a desirable manner. The materials from which substrate 10 may be fabricated should ideally themselves exhibit a low level of binding during hybridization or other events.

Figure 4:
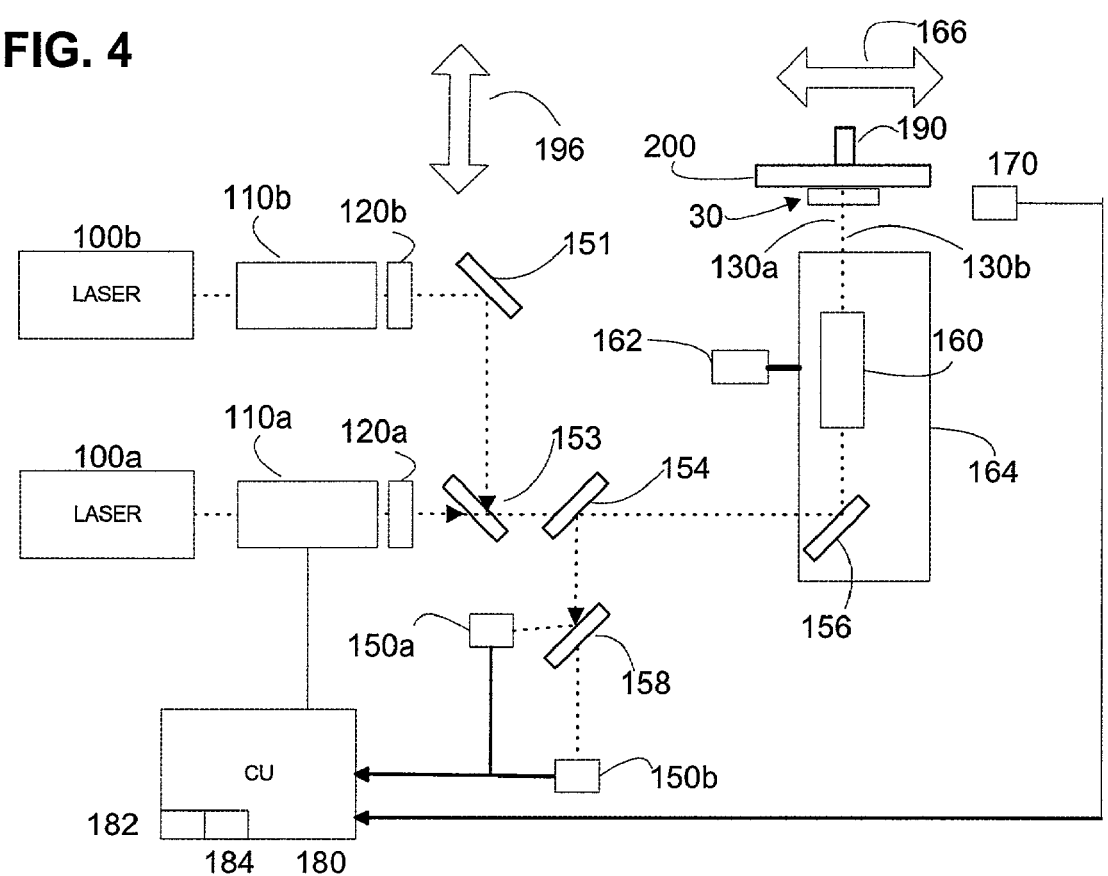
FIG. 4 schematically illustrates an apparatus of the present invention.

Referring now to FIGS. 4 and 5, an apparatus of the present invention (which may be generally referenced as an array "scanner") is illustrated. A light system provides light from a laser 100 which passes through an electro-optic modulator (EOM) 110 with attached polarizer 120. Each laser 100a, 100b may be of different wavelength (for example, one providing red light and the other green) and each has its own corresponding EOM 110a, 110b and polarizer 120a, 120b. The resulting interrogating light beams are coherent and monochormatic, and are directed along respective paths 130a, 130b toward a holder 200 by the use of full mirror 151 and dichroic mirror 153. While FIG. 4 shows these paths as being coincident for the sake of simplicity, the two may in fact be separated by an angle so as to illuminate an array at different locations as more clearly seen in FIG. 5. This angle of separation may be such that each interrogating light beam is directed along path 130a, 130b toward back surface 11b at an angle of between 0 or greater than 0, and 45 degrees to a normal to the back surface, for example less than 1 degree (such as 0.5 degrees). Such an arrangement allows the two interrogating light beams to pass through the same optical system while reducing saturation of fluorescent labels at features 16 as well as channel cross-talk. A control signal in the form of a variable voltage applied to each corresponding EOM 110a, 110b by the controller (CU) 180, changes the polarization of the exiting light which is thus more or less attenuated by the corresponding polarizer 120a, 120b. Controller 180 may be or include a suitably programmed processor. Thus, each EOM 110 and corresponding polarizer 120 together act as a variable optical attenuator which can alter the power of an interrogating light spot exiting from the attenuator. The remainder of the light from both lasers 100a, 100b is transmitted through a dichroic beam splitter 154, reflected off fully reflecting mirror 156 and focused onto an array 12 of an array unit 30 mounted on holder 200, using optical components in beam focuser 160. Light emitted, in particular fluorescence, at two different wavelengths (for example, green and red light) from features 16, in response to the interrogating light, is imaged using the same optics in focuser/scanner 160, and is reflected off mirrors 156 and 154. The two different wavelengths are separated by a further dichroic mirror 158 and are passed to respective detectors 150a and 150b. More optical components (not shown) may be used between the dichroic and each detector 150a, 150b (such as lenses, pinholes, filters, fibers etc.) and each detector 150a, 150b may be of various different types (e.g. a photo-multiplier tube (PMT) or a CCD or an avalanche photodiode (APD)). All of the optical components through which light emitted from an array 12 in response to the illuminating laser light, passes to detectors 150a, 150b, together with those detectors, form a detection system. This detection system has a fixed focal plane.

Note that, as more clearly seen in FIG. 5, both of the interrogating light beams as well as the detected emitted light, pass through substrate 10. In particular, the interrogating light beams 100a, 100b are directed along paths 130a, 130b, respectively, from the back surface 11b through substrate 10, and onto the chemical features 16a, 16n respectively, on the front surface 11a. As well, the detected emitted light passes through substrate 10 from the front surface 11a and out the back surface 11b with the detected light emitted in response to beam 100a following path 130a, and that emitted in response to beam 100b following path 130b.

A scan system causes the illuminating area in the form of a light spot from each laser 100a, 100b, and a detecting area of each detector 150a, 150b (which detecting area will form a pixel in the detected image), to be scanned across multiple an array package 30 mounted on holder 200. In this manner, each of the multiple features 16 of the array with each read feature containing multiple pixels (for example, more than five, ten, or twenty). In particular the scanning system is typically a line by line scanner, scanning the interrogating light in a line across an array 12 when at the reading position, in a direction of arrow 166, then moving ("transitioning") the interrogating light in a direction into/out of the paper as viewed in FIG. 4 to a position at an end of a next line, and repeating the line scanning and transitioning until the entire array 12 has been scanned. This can be accomplished by providing a housing 164 containing mirror 158 and focuser 160, which housing 164 can be moved along a line of pixels (that is, from left to right or the reverse as viewed in FIG. 4) by a transporter 162. The second direction 192 of scanning (line transitioning) can be provided by second transporter which may include a motor and belt (not shown) to move holder 200 along one or more tracks. The second transporter may use a same or different actuator components to accomplish coarse (a larger number of lines) movement and finer movement (a smaller number of lines). The reader of FIG. 4 may further include a reader (not shown) which reads an identifier 40 from an array package 30. When identifier 40 is in the form of a bar code, that reader may be a suitable bar code reader.

An autofocus detector 170 is also provided to sense any offset between different locations on array 12 when in the reading position, and a determined position of the focal plane of the detection system. An autofocus system includes detector 170, processor 180, and a motorized adjuster to move holder in the direction of arrow 196. A suitable chemical array autofocus system is described in pending U.S. patent application Ser. No. 09/415,184 for "Apparatus And Method For Autofocus" by Dorsel et al., filed Oct. 7, 1999, incorporated herein by reference, as well as European publication EP 1091229 published Apr. 11, 2001 under the same title and inventors.

Controller 180 of the apparatus is connected to receive signals from detectors 150a, 150b (these different signals being different "channels"), namely a signal which results at each of the multiple detected wavelengths from emitted light for each scanned pixel on array 12 when at the reading position mounted in holder 200. Controller 180 also receives the signal from autofocus offset detector 170, and provides the control signal to EOM 110, and controls the scan system. Controller 180 may also analyze, store, and/or output data relating to emitted signals received from detectors 150a, 150b in a known manner. Controller 180 may include a computer in the form of a programmable digital processor, and include a media reader 182 which can read a portable removable media (such as a magnetic or optical disk), and a communication module 184 which can communicate over a communication channel (such as a network, for example the internet or a telephone network) with a remote site (such as a database at which information relating to array package 30 may be stored in association with the identification 40). Controller 180 is suitably programmed to execute all of the steps required by it during operation of the apparatus, as discussed further below. Alternatively, controller 180 may be any hardware or hardware/software combination which can execute those steps.

In one mode of operation, the array in package 30 is typically first exposed to a liquid aqueous sample (for example, placed directly on substrate 10). The array may then be washed with buffer then water, and dried following washing then inserted into a scanner for reading. Drying may be accomplished using any suitable drying method and conditions which will not decompose the probes and their bound targets, such as any suitable one or more of: air drying at room temperature or raised temperature; reduced pressure; centrifuging; or exposure to a dry unreactive gas stream (such as dry nitrogen). Following a given array package 30 being mounted in the apparatus, the identifier reader may automatically (or upon operator command) read array ID 40, and use this to retrieve information on the array layout as well as an instruction that the array should be interrogated and read through the substrate from the back surface. Such information may be retrieved directly from the contents of identifier 40 when ID 40 contains such information. Alternatively, identifier 40 may be used to retrieve such information from a database containing the identifier in association with such information. Such a database may be a local database accessible by controller 180 (such as may be contained in a portable storage medium in drive 182 which is associated with package 30, such as by physical association with package 30 when received by the user, or by a suitable identification), or may be a remote database accessible by controller 180 through communication module 184 and a suitable communication channel (not shown). The retrieved instruction on how the array should be interrogated and read, can be used by controller 180 to check that the array is oriented within an array reader such that the array can be interrogated and read by the reader through the substrate from the back surface. Controller 180 may do this based on the orientation of identifier 40 in holder 200. This may be done by checking whether the identifier 40 is facing focuser 160 or not. To determine this, two identifier readers may be provided facing respective surfaces 11a, 11b of a mounted substrate 10, such that each will only be able to read identifiers (or some other indicia on one side 11a or 11b only) on the side 11a or 11b which it faces. Controller 180, knowing that the read identifier is on a particular side of substrate 10 (which information can also be retrieved in the manner earlier described, based on the identifier), and which identifier reader successfully read the identifier, can determine the orientation of the mounded substrate 10 in the array reader.

The saved results from a sample exposed array, read according to a method of the present invention, may be raw results (such as fluorescence intensity readings for each feature in one or more color channels) or may be processed results such as obtained by rejecting a reading for a feature which is below a predetermined threshold and/or forming conclusions based on the pattern read from the array (such as whether or not a particular target sequence may have been present in the sample). The results of the reading (processed or not) may be forwarded (such as by communication of data representing the results) to a remote location if desired, and received there for further use (such as further processing).

Figure 6:
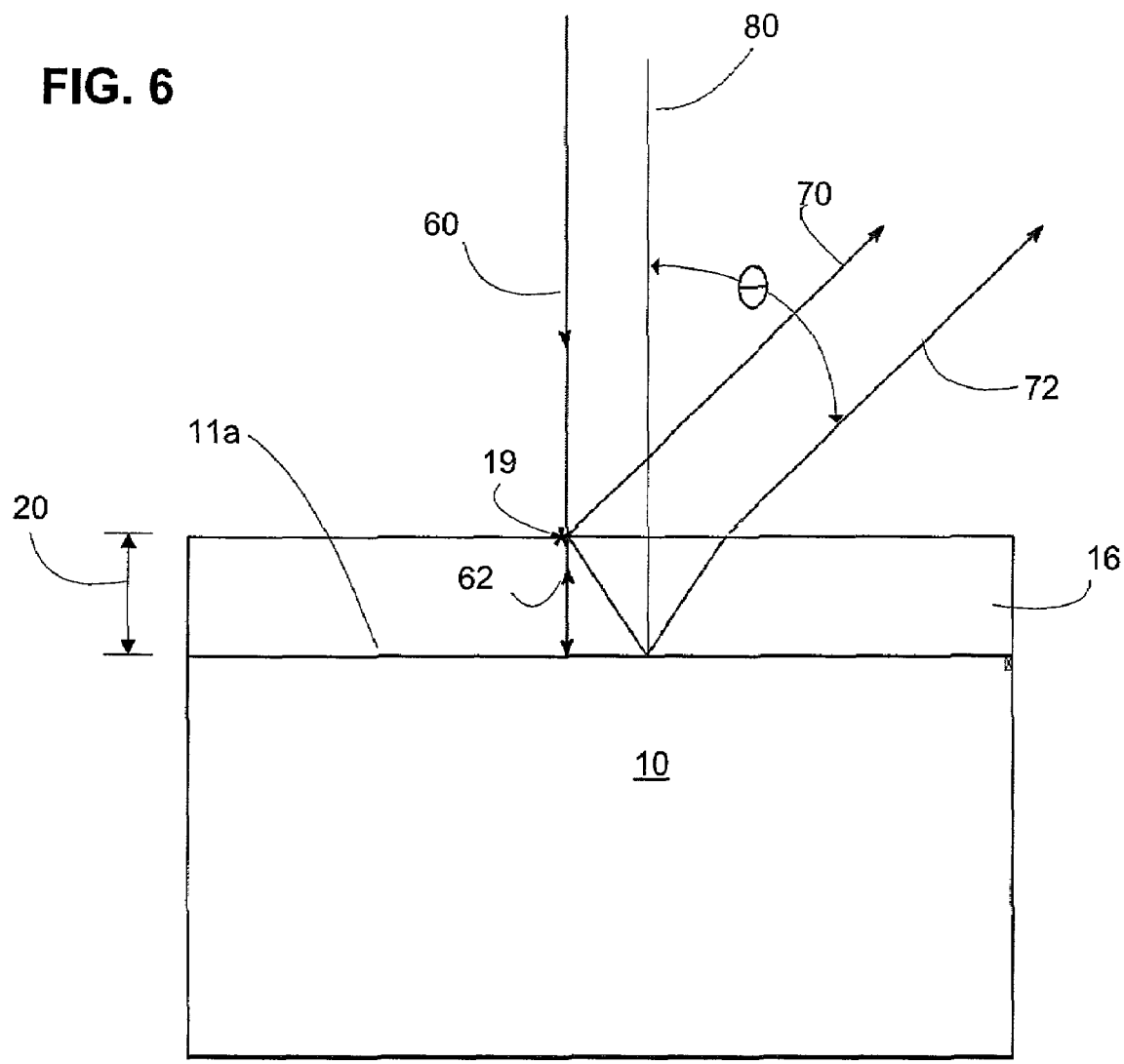
FIG. 6 illustrates a conventional illumination and signal detection (not of the present invention) of a dry array from a forward direction.

An advantage of interrogating and reading a dry array dry through the substrate 10, can be understood with reference to FIG. 6 which illustrates a conventional reading of a dry array from the front surface 11a. For a conventional scanning of a dry slide as shown in FIG. 6, an interrogating beam may be incident at (close to) normal incidence to the substrate surface 11a. The fluorescent molecular group 19 to be detected will then be exposed to the interference of the incident wave 60 and the reflected wave 62. For scanning from the front side these will typically interfere in a way that reduces the overall electric field strength seen by the molecule for a glass substrate to about 80% of its value for illuminating an isolated molecule in empty space. Typically, the path difference between these waves 60 and 62 is small compared to the coherence length of the laser light used for scanning. For larger angles the reduction effect my be reduced and depending on polarization revert at angles above 45 degrees.

Detected light is collected typically from angles between 0 degrees from the normal of surface 11a and a fixed, preferably large angle. FIG. 6 illustrates both detected light 70 which is emitted directly from group 19 at an angle θ to a normal 80 to surface 11a, and light 72 which may be reflected from front surface 11a and can therefore destructively interfere with light 70. While the same dependence on angle and polarization exists as for the illuminating light, the average over polarizations and directions will again show a significant reduction over the situation of an isolated molecule.

A reduction of the field to about 80% (for a glass substrate) corresponds to a reduction of the resulting light power and energies to about 64% as these are proportional to the square of the field. The combined effects of the foregoing disadvantageous (partially destructive) interference would reduce the light detected overall (multiplying the reductions of illumination and light collection) to about 41% of the value for an isolated molecule. As scanning from the back side and through the substrate causes Fresnel reflection losses from passing the illuminating and collected light through two substrate interfaces each, the overall disadvantage of front side scanning over back-side scanning is a little less and has been measured to be about 50% or a factor of 2 for a glass substrate. This can be seen more clearly in the following where one assumes the following values: a reflectivity ("R") of 0.04, an incident power ("$P_0$") of 100%, and an initial fluorescence ("$F_0$") of 100%. The illumination power, $P_B$, at a feature on the front side 11a of substrate, when illuminating through the substrate is given by:

$$P_B = P_0(1-R)^2 \tag{1}$$

On the other hand the illumination power, $P_F$, on the front side 11a when illuminating from the front side without going through the substrate and with resulting destructive interference of the illuminating light is given by (assuming a zero distance form the front side):

$$P_F = P_0(1-\sqrt{R})^2 \tag{2}$$

Similarly, the emitted fluorescence, $F_B$, which can be detected through the substrate is given by equation (3) below, while the emitted fluorescence, $F_F$, which can be detected without going through the substrate and assuming destructive interference is given by equation (4) below:

$$F_B = F_0(1-R)^2 \tag{3}$$

$$F_F = F_0(1-\sqrt{R})^2 \tag{4}$$

Note that a variety of geometries of the features 16 may be constructed other than the organized rows and columns of the array of FIGS. 1–3. For example, features 16 can be arranged in a series of curvilinear rows across the substrate surface (for example, a series of concentric circles or semi-circles of spots), and the like. Even irregular arrangements of features 16 can be used, at least when some means is provided such that during their use the locations of features of particular characteristics can be determined (for example, a map of the features is provided to the end user with the array). Furthermore, substrate 10 could carry more than one array 12, arranged in any desired configuration on substrate 10. While substrate 10 is planar and rectangular in form, other shapes (for example, circular) could be used with housing 34 being adjusted accordingly. In many embodiments, substrate 10 will be shaped generally as a planar, rectangular solid, having a length in the range about 4 mm to 200 mm, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. However, larger substrates can be used. Less preferably, substrate 10 could have three-dimensional shape with irregularities in first surface 11*a*. In any event, the dimensions of housing 34 may be adjusted accordingly. Additionally, during scanning it is possible to illuminate all pixels of a line simultaneously (for example, by using a line of light emitting diodes).

Other various modifications to the particular embodiments described above are, of course, possible. Accordingly, the present invention is not limited to the particular embodiments described in detail above.

What is claimed is:

1. A method of interrogating an addressable array unit having a transparent substrate with a back surface, and an array with a plurality of different chemical features on a front surface, the method comprising:
   (a) illuminating the features while the array is dry, with an interrogating light which is directed through the substrate from the back surface and onto the chemical features on the front surface; and
   (b) detecting light emitted from respective features in response to the interrogating light, which detected light has passed from the front surface, through the substrate and out the back surface;
   wherein the light is emitted from locations of the features which are spaced from the front surface a distance of less than one-eighth of the wavelength of the illuminating light in a gas or a vacuum which is in contact with the dry array.

2. A method according to claim 1 wherein the light emitting locations of the chemical features are spaced from the front surface a distance of less than one-tenth of the wavelength of the illuminating light.

3. A method according to claim 1 wherein the tight emitting locations of the chemical features are spaced from the front surface a distance of less than one-twentieth of the wavelength of the illuminating light.

4. A method according to claim 1 wherein the light emitting locations of the chemical features are spaced from the front surface a distance of less than one-fiftieth of the wavelength of the illuminating light.

5. A method according to claim 1 wherein the interrogating light is directed toward the back surface at an angle of between 0 and 45 degrees to a normal to the back surface.

6. A method according to claim 5 wherein the angle is less than 25 degrees.

7. A method according to claim 5 wherein the angle is less than 10 degrees.

8. A method according to claim 1 wherein the chemical features are polynucleotides.

9. A method according to claim 1 wherein the chemical features are amino acid polymers.

10. A method of interrogating an addressable array unit having a transparent substrate with a back surface, and an array with a plurality of different chemical features on a front surface, the method comprising:
    (a) illuminating the features while the army is dry, with an interrogating light which is directed through the substrate from the back surface and onto the chemical features on the front surface; and
    (b) detecting light emitted from respective features in response to the interrogating light, which detected light has passed from the front surface, through the substrate and out the back surface;
    wherein the light is emitted from locations of the features which are spaced from the front surface a distance of less than one-eighth of the wavelength of the emitted light in a gas or a vacuum which is in contact with the dry array.

11. A method according to claim 10 wherein the light is emitted from locations of the features which are spaced from the front surface a distance of less than one-tenth of the emitted light wavelength.

12. A method according to claim 10 wherein the light is emitted from locations of the features which are spaced from the front surface a distance of less than one-fiftieth of the emitted light wavelength.

13. A method according to claim 1 additionally comprising, prior to the illuminating and detecting:
    exposing the array to a sample in a liquid; and
    washing and drying the array.

* * * * *